(12) United States Patent
Tokita et al.

(10) Patent No.: US 8,876,717 B2
(45) Date of Patent: Nov. 4, 2014

(54) BIOLOGICAL INFORMATION ACQUISITION APPARATUS

(75) Inventors: Toshinobu Tokita, Yokohama (JP);
Kazuhiko Fukutani, Yokohama (JP);
Takao Nakajima, Kawasaki (JP);
Katsumi Nakagawa, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/140,866

(22) PCT Filed: Dec. 16, 2009

(86) PCT No.: PCT/JP2009/071368
§ 371 (c)(1),
(2), (4) Date: Jun. 20, 2011

(87) PCT Pub. No.: WO2010/074103
PCT Pub. Date: Jul. 1, 2010

(65) Prior Publication Data
US 2011/0257530 A1    Oct. 20, 2011

(30) Foreign Application Priority Data

Dec. 25, 2008 (JP) .................................. 2008-330364
Oct. 16, 2009 (JP) .................................. 2009-239399

(51) Int. Cl.
*A61B 8/00* (2006.01)
*A61B 8/14* (2006.01)
*A61B 5/00* (2006.01)
*A61B 8/08* (2006.01)

(52) U.S. Cl.
CPC .............. *A61B 8/0825* (2013.01); *A61B 5/4312* (2013.01); *A61B 5/0091* (2013.01); *A61B 5/0095* (2013.01)

USPC ........................... 600/443; 600/437; 600/438

(58) Field of Classification Search
None
See application file for complete search history.

(56) References Cited

U.S. PATENT DOCUMENTS

| 5,713,356 A | * | 2/1998 | Kruger .......................... 600/407 |
| 5,999,836 A | | 12/1999 | Nelson et al. |
| 6,607,489 B2 | | 8/2003 | Hoctor et al. |
| 2002/0099290 A1 | | 7/2002 | Haddad |

(Continued)

FOREIGN PATENT DOCUMENTS

| JP | 62-025260 A | 2/1987 |
| JP | 2005125080 A | 5/2005 |

(Continued)

OTHER PUBLICATIONS

Manohar et al., "The Twente Photoacoustic Mammoscope: System Overview and Performance," Biophysical Engineering Group, May 18, 2005, vol. 50, pp. 2543-2557.

*Primary Examiner* — Long V. Le
*Assistant Examiner* — Farshad Negarestan
(74) *Attorney, Agent, or Firm* — Canon USA Inc. IP Division

(57) ABSTRACT

When a subject is pressed by a plate and an acoustic wave is received by a probe via the plate, the acoustic wave is refracted because of the difference between a sound velocity in the subject and a sound velocity in the plate. When the refraction is not considered, a reduction in resolution occurs. A correction table or a correction formula for correcting image distortion associated with refraction is provided. After image information is acquired, new image information is acquired in accordance with the correction table or the correction formula, and is displayed.

12 Claims, 10 Drawing Sheets

(56) References Cited

U.S. PATENT DOCUMENTS

2006/0056580 A1 3/2006 Frangioni et al.
2006/0184042 A1 8/2006 Wang et al.
2006/0235302 A1 10/2006 Grossman et al.
2008/0242979 A1 10/2008 Fisher et al.

FOREIGN PATENT DOCUMENTS

| JP | 2008-079835 A | 4/2008 |
|---|---|---|
| WO | 0126555 A | 4/2001 |
| WO | 2007/025278 A2 | 3/2007 |

* cited by examiner

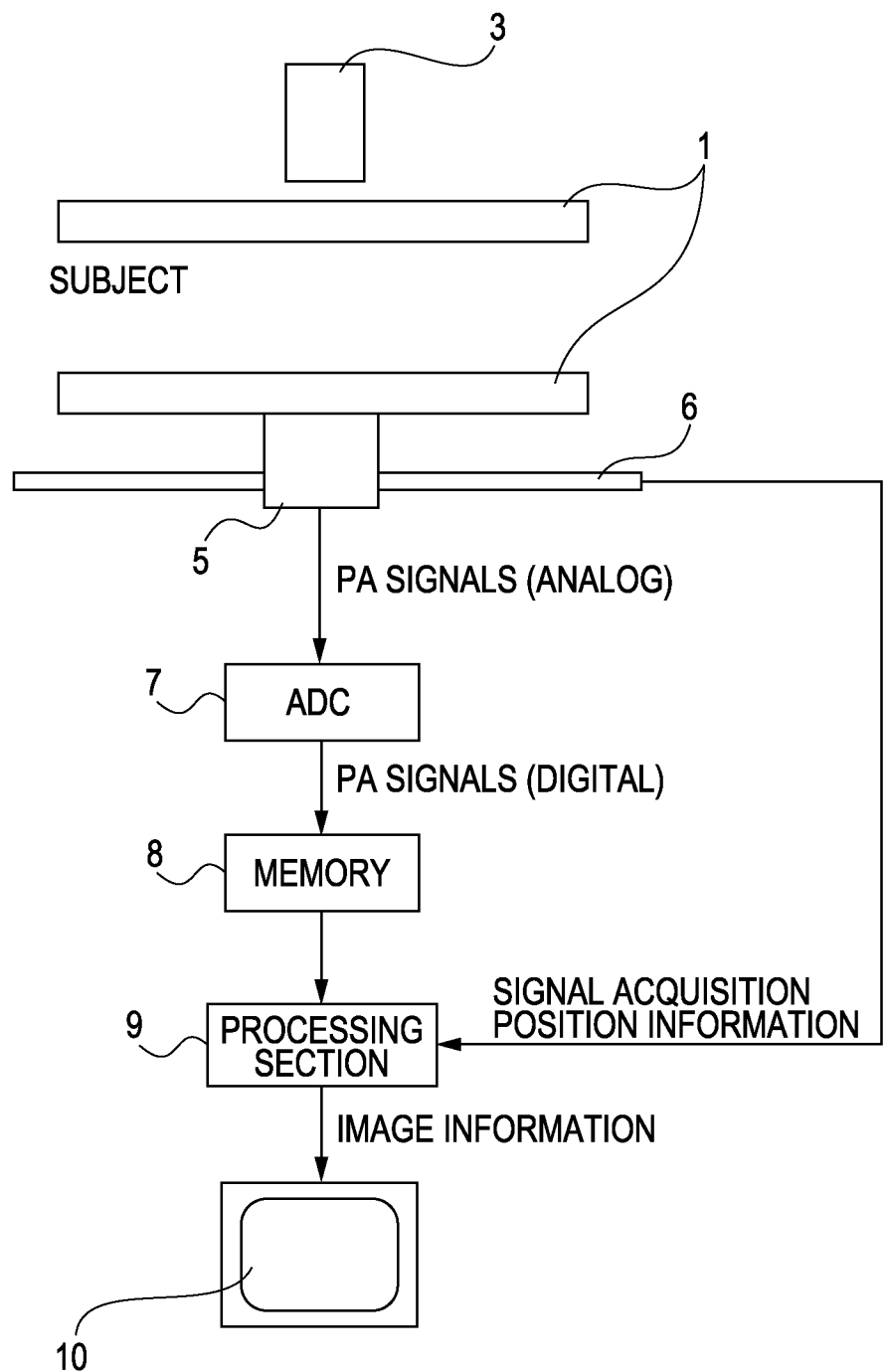

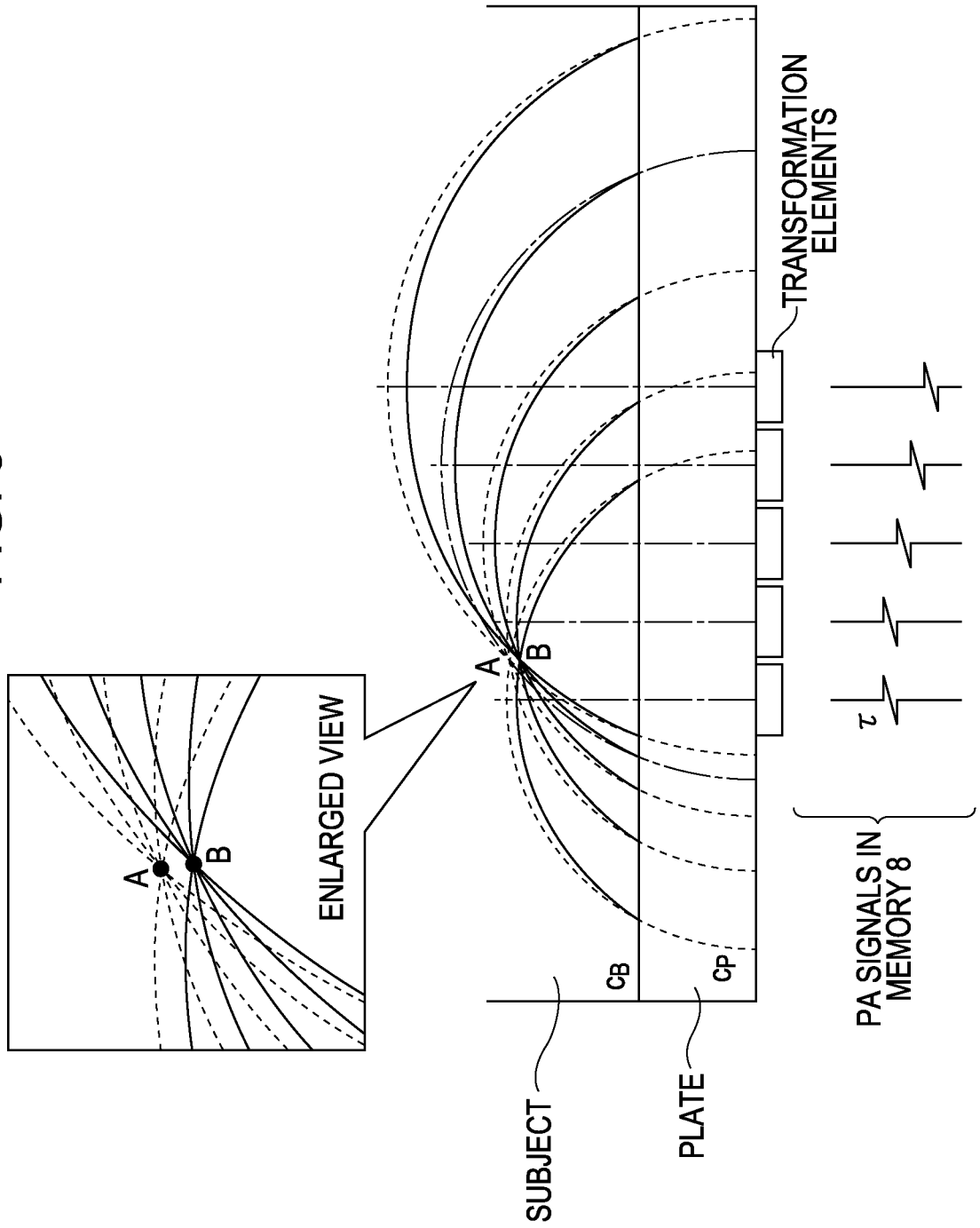

BIOLOGICAL INFORMATION ACQUISITION APPARATUS

TECHNICAL FIELD

The present invention relates to a biological information acquisition apparatus for performing imaging using an acoustic wave that is emitted from a subject.

BACKGROUND ART

There is a photoacoustic apparatus that has been developed for breast cancer screening as a biological information acquisition apparatus of the related art that is described in Non Patent Citation. The biological information acquisition apparatus that is described in Non Patent Citation presses a subject (a breast) with a glass plate and an ultrasound probe, and irradiates the subject via the glass plate with illumination light (near-infrared light) that is emitted from a light source which is an Nd:YAG laser. Then, the biological information acquisition apparatus receives, with the probe, a photoacoustic wave that is an acoustic wave generated inside the subject, and generates and displays an image of tissue inside the subject, in particular, an image of breast cancer angiogenesis. An operation for image generation in such a manner is called image reconstruction. Note that a polymer with a thickness of 18.6 mm is provided on the surface of the probe. Because a sound velocity of a sound propagating through the polymer is different from a sound velocity of a sound propagating through the subject, the photoacoustic wave is refracted by the polymer before the photoacoustic wave is received by the probe. When refraction of the photoacoustic wave is not considered in image reconstruction, a reduction in resolution occurs.

A method for solving the above-mentioned issue is described in Patent Citation. In Patent Citation, a multifunction apparatus in which an X-ray mammography and an ultrasound apparatus are combined together is described. The X-ray mammography presses a subject using a compression plate that is used as a subject holding member, obtains information concerning X-rays by causing the X-rays to pass through the subject, and performs imaging in accordance with the information concerning X-rays. When the ultrasound apparatus is combined with the X-ray mammography, an ultrasound probe transmits/receives an ultrasound wave via the compression plate. FIG. 9 illustrates a state in which the ultrasound wave is refracted when the ultrasound wave enters the compression plate. Accordingly, referring to FIG. 9, delay times are calculated in accordance with Equations (101) to (104) so that refraction of the ultrasound wave which occurred due to the difference between the sound velocity in the compression plate and the sound velocity in the subject is corrected. Signals that are obtained by individual transformation elements are added to one another. T is an arrival time of the ultrasound wave. $c_1$ and $c_2$ are a sound velocity of a sound propagating through the compression plate and a sound velocity of a sound propagating through the subject, respectively. $L_1$, $L_2$, $R_1$, $R_2$, and D denote individual distances shown in FIG. 9. $\beta_1$ and $\beta_2$ are angles shown in FIG. 9. Note that Equation (104) is not clearly described in Patent Citation.

$$T = \frac{L_1}{c_1} + \frac{L_2}{c_2} \quad (101)$$

-continued $$\beta_1 = \sin^{-1}\left(\frac{c_1}{c_2}\sin\beta_2\right) \quad (102)$$

$$T = \frac{R_1}{c_1\cos\beta_1} + \frac{R_2}{c_2\cos\beta_2} \quad (103)$$

$$D = R_1\tan\left[\sin^{-1}\left(\frac{c_1}{c_2}\sin\beta_2\right)\right] + R_2\tan\beta_2 \quad (104)$$

PATENT CITATION

U.S. Pat. No. 6,607,489

NON PATENT CITATION

Srirang Manohar, et al., The Twente photoacoustic mammoscope: system overview and performance, Physics in Medicine and Biology 50 (2005) 2543-2557

DISCLOSURE OF INVENTION

Correction for refraction in image reconstruction is not described in Non Patent Citation. The photoacoustic wave that is emitted from the subject is refracted by the polymer, and this leads to a reduction in resolution. Patent Citation aims to solve the above-mentioned issue. However, in the multifunction apparatus described in the Patent Citation, it is necessary to calculate an angle of refraction using simultaneous equations or in an analytical manner when addition of the signals to one another is performed. Thus, this leads to an increase in a calculation time taken to acquire image information.

The present invention aims to solve the above-mentioned issues of the background art. The present invention provides a biological information acquisition apparatus in which a reduction in resolution associated with refraction of an ultrasound wave that occurred between a subject and a subject holding member is suppressed, and in which a calculation time is reduced.

In order to achieve the above-mention aim, a biological information acquisition apparatus according to an aspect of the present invention includes the following: a probe configured to receive an acoustic wave emitted from a subject and to convert the acoustic wave into electric signals; a subject holding member provided between the subject and the probe; and a processing section configured to acquire image information using the electric signals. The processing section has at least a correction table or a correction formula for performing correction for refraction of an acoustic wave that has occurred due to a difference between a sound velocity in the subject and a sound velocity in the subject holding member. The processing section corrects, on an image-element-by-image-element basis in accordance with the correction table or the correction formula, image information which is acquired using the electric signals and in which refraction is not considered, thereby acquiring new image information.

According to the aspect of the present invention, the new image information is acquired in accordance with the correction table or the correction formula, whereby a reduction in resolution associated with refraction of the acoustic wave that occurred between the subject and the subject holding member is suppressed, so that resolution can be improved. Furthermore, when the signals are added to one another, a calculation time can be reduced, compared with a method which is described in Background Art and in which an angle of refraction is calculated using simultaneous equations or in an analytical manner.

BRIEF DESCRIPTION OF DRAWINGS

FIG. 2A is a schematic diagram for explaining a signal processing section in the first embodiment of the present invention.

FIG. 6 is a schematic diagram for explaining a circular-back-projection in the first embodiment of the present invention.

DESCRIPTION OF EMBODIMENTS

Figure 1:
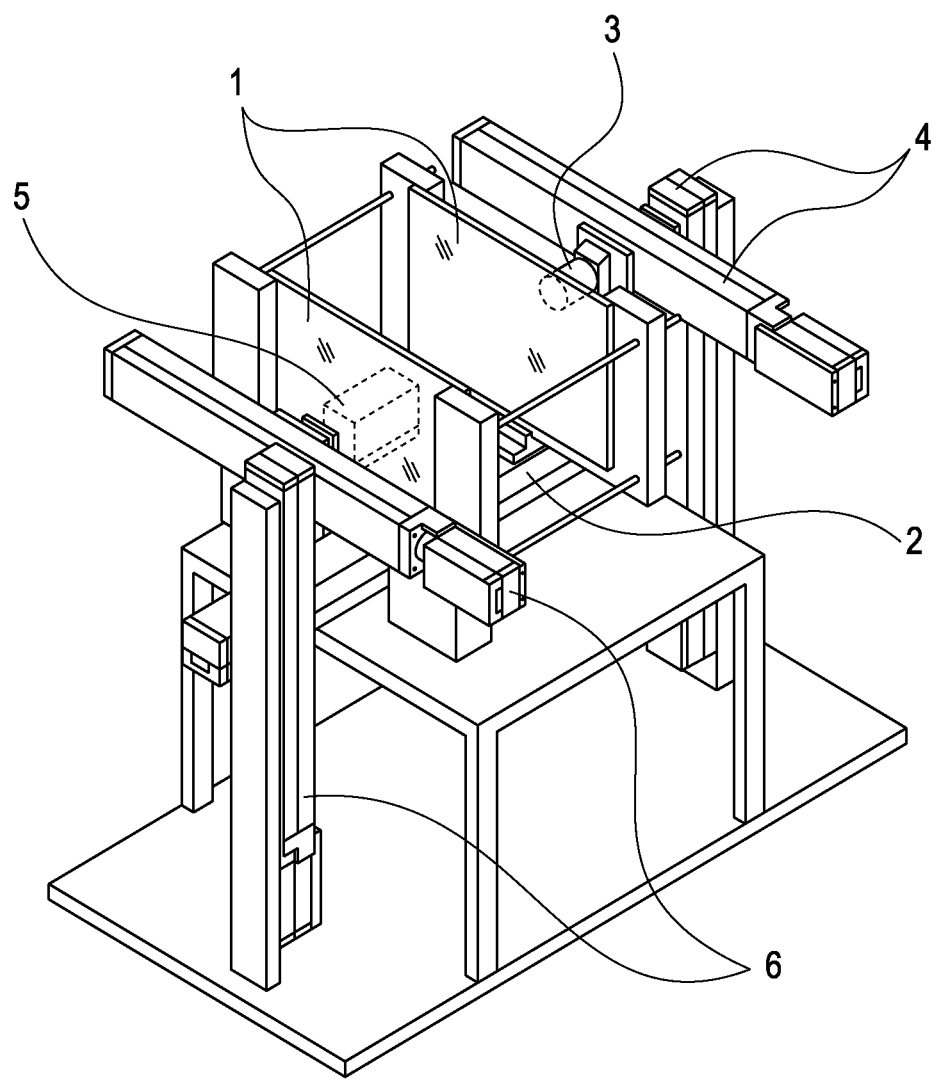
FIG. 1 is a schematic diagram for explaining a system configuration of a photoacoustic mammography apparatus according to a first embodiment of the present invention.

When a subject holding member is provided between a subject and a probe that receives an acoustic wave, refraction of the acoustic wave can be geometrically determined in accordance with Snell's law using a thickness of the subject holding member, a sound velocity of a sound propagating through the subject holding member, and a sound velocity of a sound propagating through the subject. Then, amounts of transformation in positions of individual image elements are calculated, and stored as a correction table or a correction formula. After that, image information that is acquired without consideration of refraction is corrected by transforming positions of the image elements in accordance with the correction table or the correction formula, thereby acquiring new image information. In other words, the new image information is image information in which refraction is considered.

Note that examples of an acoustic wave in embodiments of the present invention include a wave called a sound wave, a wave called an ultrasound wave, and a wave called a photoacoustic wave. For example, the examples of an acoustic wave include a photoacoustic wave that is generated inside a subject by irradiating the inside of the subject with light such as near-infrared light, and an ultrasound wave that is transmitted to the inside of a subject and that is reflected. Furthermore, the examples of an acoustic wave emitted from a subject include an acoustic wave that is reflected by at least one portion of the subject, and an acoustic wave that is generated by the portion of the subject. In other words, examples of biological information acquisition apparatuses according to the embodiments of the present invention include the following apparatuses: a photoacoustic apparatus that irradiates the inside of a subject with light, that receives, using a probe, a photoacoustic wave which is generated inside the subject, and that displays an image of tissue of the inside of the subject; and an ultrasound apparatus that transmits/receives an ultrasound wave to/from the inside of a subject, and that displays an image of tissue of the inside of the subject. A probe includes a plurality of transformation elements that receive an acoustic wave and that convert the acoustic wave into signals (electric signals). A subject holding member is provided between a subject and a probe, and holds the shape of at least one portion of the subject. Examples of the subject holding member include a member called a compression plate, a member called a parallel flat plate, and a member called a plate. The surface of the subject holding member may have a curvature.

Hereinafter, the embodiments of the present invention will be described. Note that, in the first embodiment, an image reconstruction method and a photoacoustic mammography (hereinafter, referred to as "PAM") apparatus in which refraction of a photoacoustic wave is considered will be described. The image reconstruction method and the PAM apparatus are PAMs using a photoacoustic tomography (hereinafter, referred to as "PAT") as a principle. Then, in the second embodiment, an example in which refraction of an ultrasound wave is considered in an ultrasound apparatus will be described.

First Embodiment

FIG. 1 is a schematic diagram of a configuration of a PAM apparatus. Using photoacoustic waves, because an image of blood or blood vessels can be distinctively acquired, an image of cancer angiogenesis can be picked up. FIG. 1 shows the configuration in which this principle is applied to breast cancer screening.

Referring to FIG. 1, plates 1 are parallel flat plates that fix a subject. A compression mechanism 2 drives the two plates 1 so as to relatively move the plates 1 toward or away from each other. The plates 1 and the compression mechanism 2 are used to insert the subject (a breast) between the plates 1, and to press the subject. Note that, although a robot mechanism that performs automatic compression is illustrated as the compression mechanism 2, the compression mechanism 2 is not limited thereto. The compression mechanism 2 may be an air cylinder mechanism, a vise mechanism, or compression may be manually performed using a rack and pinion, worm gears, and so forth.

An illumination optical system 3 is an optical system for irradiating the subject with laser light having a wavelength that is approximately in the range of 700 nm to 1100 nm in order to cause the subject to generate a photoacoustic wave. Note that a propagation path of illumination light from a laser light source to the illumination optical system 3 is not illustrated. An illumination-light scan section 4 causes the illumination optical system 3 to perform scanning. A probe 5 is an acoustic-wave transducer that receives a photoacoustic wave which is generated by the subject. A probe scan section 6 causes the probe 5 to perform scanning.

A translucent resin, such as an acrylic resin or a polycarbonate resin, or an inorganic material, such as a quartz glass, is suitable as the material of the plate 1 at the side of the illumination optical system 3, which is one of the plates 1. In order to perform acoustic impedance matching in a path from the subject to the probe 5, a resin is suitable as the material of the plate 1 used as a subject holding member at the side of the probe 5, which is the other one. More particularly, polymethylpentene is suitable.

Next, a configuration will be described, in which a process sequence from reception of a photoacoustic wave with the probe 5 to performance of image reconstruction is realized. FIG. 2A is a diagram illustrating a signal flow of the process sequence from detection of a photoacoustic wave with the probe 5 to imaging of biological information concerning the subject using the photoacoustic wave. Referring to FIG. 2A, an analog-to-digital converter (ADC) 7 digitizes analog signals that the probe 5 has received, thereby obtaining digital signals. Note that, preferably, an amplifier for amplifying signals is provided between the probe 5 and the ADC 7. For example, the amplifier may be embedded in the probe 5. A memory 8 is a section that temporarily stores the digital signals. A processing section 9 performs a filtering process for noise reduction, and performs image reconstruction in accordance with signal acquisition position information that is supplied from the probe scan section 6. A display section 10 displays image information that is acquired by image reconstruction performed by the processing section 9.

Figure 2B:
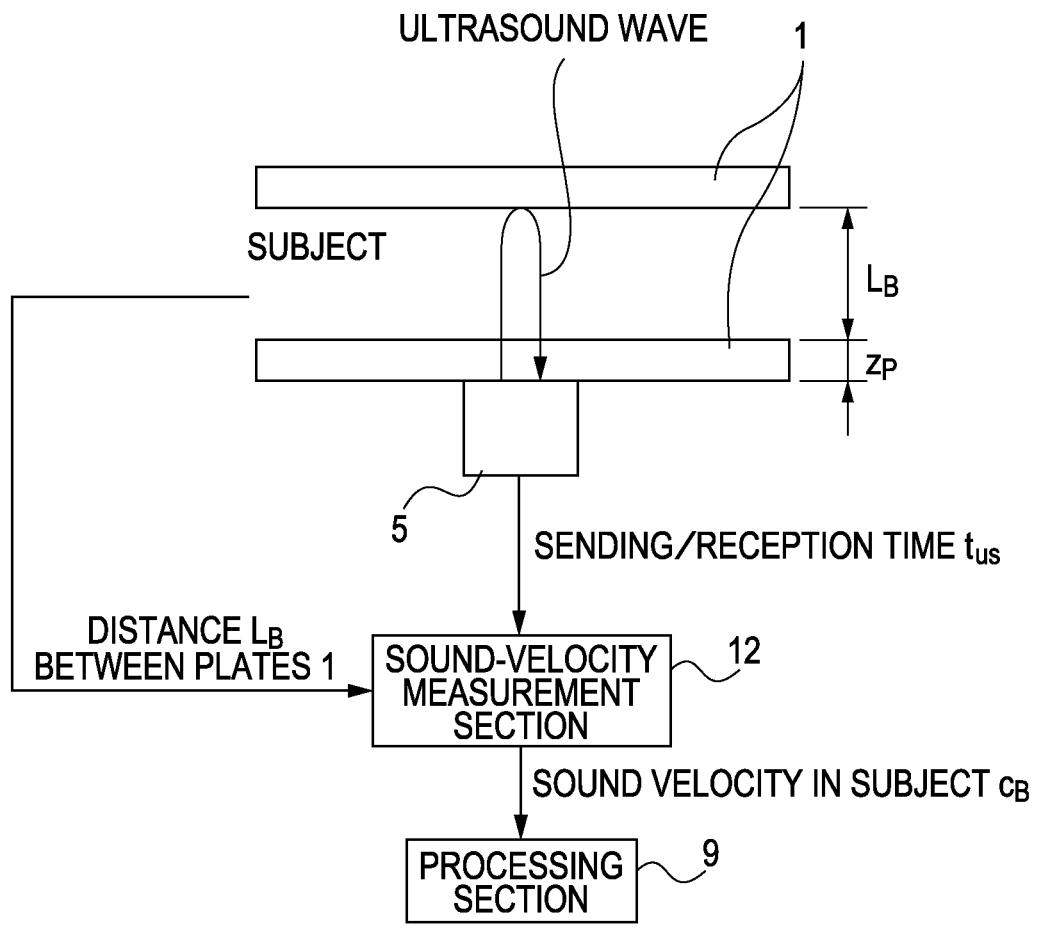
FIG. 2B is a schematic diagram for explaining the signal processing section in the first embodiment of the present invention.

In the PAM apparatus that is described with reference to FIG. 1 and FIG. 2A, a sound velocity of a sound propagating through the subject is different from a sound velocity of a sound propagating through the plate. Accordingly, the photoacoustic wave is refracted at an interface between the subject and the plate. For example, the sound velocity in the subject is about 1540 m/s (about 1510 m/s in a breast). When the material of the plate 1 is polymethylpentene, the sound velocity in the plate 1 is about 2200 m/s. The numerical value given above can be used as the sound velocity in the subject. However, preferably, a sound velocity is measured by a sound-velocity measurement section 12 in advance, and the measured sound velocity is used when a correction table or a correction formula, which are described below, is determined. As shown in FIG. 2B, the sound-velocity measurement section 12 can measure the sound velocity in the subject using a method for, for example, calculating a sound velocity using a time $t_{us}$, which is a time from when an ultrasound wave is transmitted from the probe 5 to the subject sandwiched between the plates 1 to when the reflected ultrasound wave is received, and using a distance $L_B$ between the two plates 1. Note that, in a case of FIG. 2B, a sound velocity $c_B$ in the subject can be calculated using $c_B = L_B/(t_{us}/2 - z_p/c_p)$ because a thickness $z_p$ of the plate 1 and a sound velocity $c_p$ in the plate 1 are known.

Figure 3:
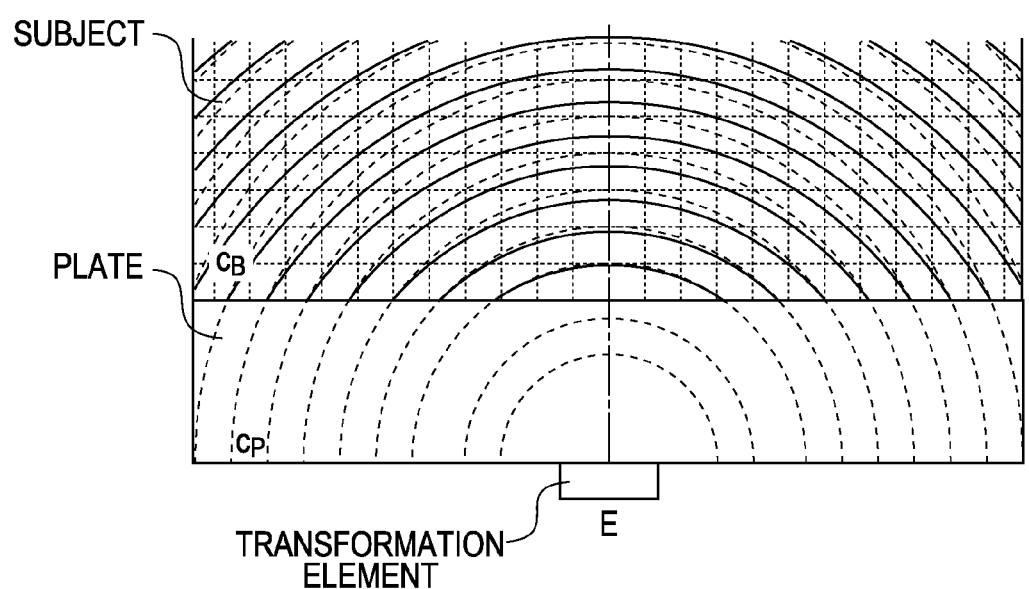
FIG. 3 is a schematic diagram for explaining image distortion associated with refraction in the first embodiment of the present invention.

FIG. 3 illustrates a state in which an ultrasound wave that is an acoustic wave expands with respect to a transformation element of the probe 5. In the present invention, an image element is a pixel or voxel. Note that, for simplicity of description, states in two dimensions are described with reference to FIG. 3 and the following drawings. However, the dimensions are not limited to two dimensions. The dimensions can be extended to three dimensions. Accordingly, in the description given below, an "image element" is denoted by a "voxel".

In image reconstruction of the related art, calculation is performed under the assumption that a photoacoustic wave is a spherical wave. Referring to FIG. 3, when it is supposed that the sound velocity in the subject is equal to the sound velocity in the plate 1, the broken lines indicate wavefronts of a photoacoustic wave that is a spherical wave. However, in reality, because the sound velocity in the subject is lower than the sound velocity in the plate 1, the photoacoustic wave is refracted. Wavefronts of the refracted photoacoustic wave are indicated by the solid lines.

In other words, after image reconstruction using an image reconstruction method of the related art is performed, individual voxels are distorted in directions from the wavefronts indicated by the broken lines shown in FIG. 3 to the wavefronts indicated by the solid lines, whereby correction can be performed for refraction of the photoacoustic wave. That is, image information that has been acquired without consideration of refraction is corrected on a voxel-by-voxel basis. Note that, although FIG. 3 illustrates a state in which an ultrasound wave is transmitted, a state in which an ultrasound wave is received can also be described in the same manner.

Figure 4:
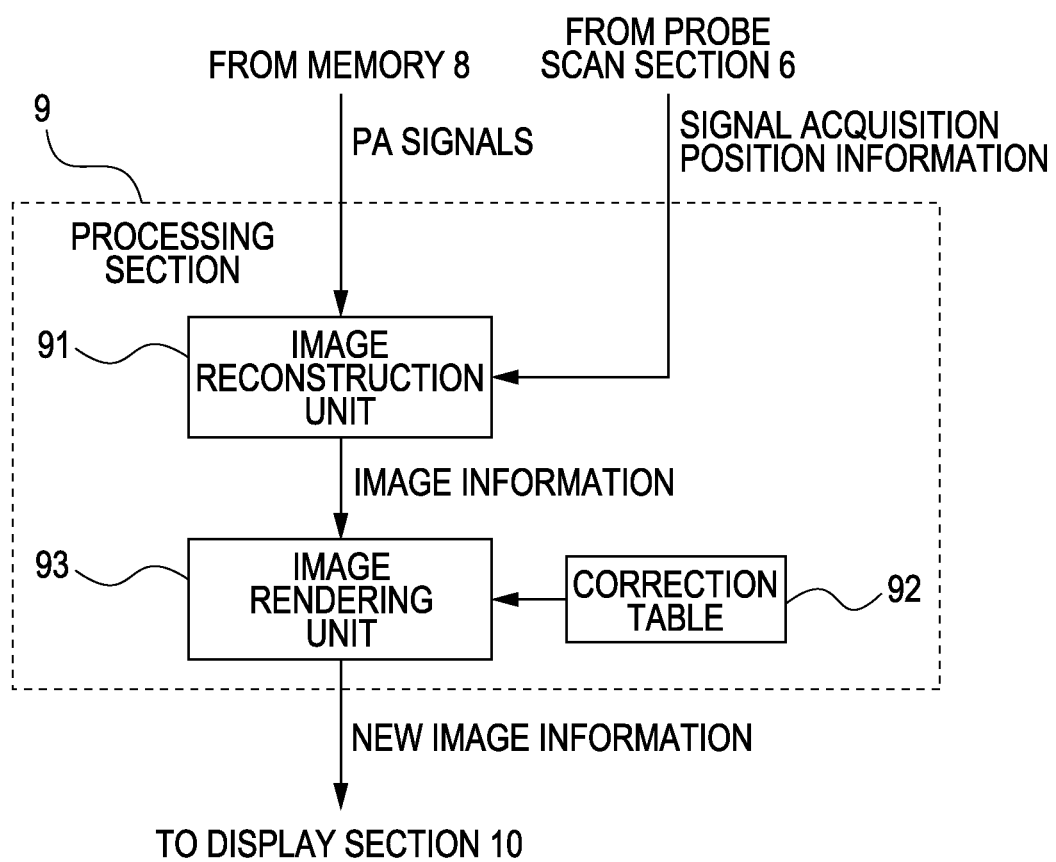
FIG. 4 is a schematic diagram for explaining a processing unit that acquires new image information in the first embodiment of the present invention.

Accordingly, as shown in FIG. 4, an image reconstruction unit 91, a correction table 92, and an image rendering unit 93 are provided in the processing section 9. The image reconstruction unit 91 performs calculation using the image reconstruction method of the related art in accordance with information concerning PA signals supplied from the memory 8 and signal acquisition position information supplied from the probe scan section 6. In the image reconstruction method of the related art, a time-domain algorithm, such as a delay-and-sum or a circular-back-projection, or a Fourier-domain algorithm is used. In this case, as in the case of Patent Citation described in Background Art, it is not necessary to consider, in the calculation, refraction of a photoacoustic wave that occurred at the interface between the plate 1 and the subject. In other words, when image information that has been acquired in this state is displayed, the shape of a generating source that generated the photoacoustic wave is distorted. In order to correct the distortion of the generating source, the correction table 92 is provided in the first embodiment of the present invention. Because an amount of distortion differs depending on a distance from a transformation element E of the probe 5, the correction table 92 can be provided as a table in which the amounts of distortion are summarized.

Figure 5A:
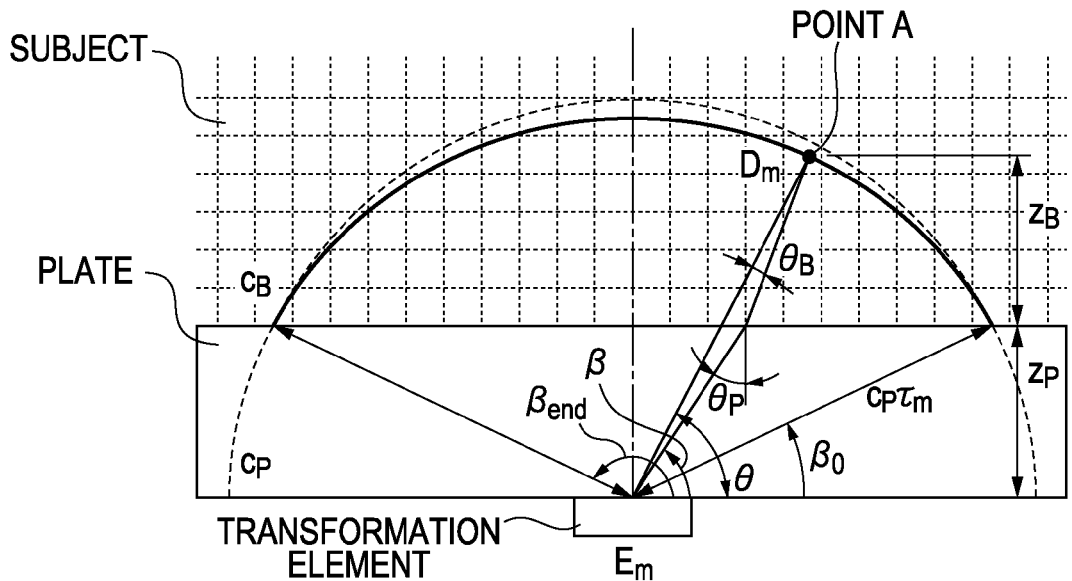
FIG. 5A is a schematic diagram for explaining image distortion associated with refraction using equations in the first embodiment of the present invention.

The correction table 92 will be described with reference to FIG. 5A. For example, regarding the voxels through which a curve indicated by a solid line (a continuous line on which a point A moves), $D_m$ that is a distance from a transformation element $E_m$ can be represented by a function using $\theta$. The curve from $\beta_0 = \sin^{-1}(z_p/c_p\tau_m)$ to $\beta_{end} = \pi - \beta_0$, on which the point A moves, is determined. $z_p$ is the thickness of the plate 1, and $c_p$ is the sound velocity in the plate 1. Because both $z_p$ and $c_p$ are known, a distance from the transformation element $E_m$ to the interface between the plate 1 and the subject can be determined. Accordingly, a propagation time $\tau_p$ taken for a photoacoustic wave to propagate through the distance can be calculated. Then, an angle of refraction can be calculated using Snell's law $\theta_B = \sin^{-1}(\sin \theta_P \cdot c_B/c_P)$. An arrival time $\tau_m$ of the photoacoustic wave is determined using an acquired PA signal. A time taken $\tau_B$ for the photoacoustic wave to pass through the subject can be calculated using $\tau_B = \tau_m - \tau_p$. A point that is determined by extending a line from the interface between the plate 1 and the subject by $c_B \cdot \tau_B$ in a direction of the angle of refraction can be determined as the point A. Furthermore, when the point A is determined, an angle $\theta$ defined by a straight line from the point A to the transformation element $E_m$, and $D_m$ that is a distance from the transformation element $E_m$ to the point A can be calculated. In this manner, $D_m$ can be represented by a function using $\theta$ ($D_m(\theta)$). Moreover, when image reconstruction is performed without consideration of refraction, an image is positioned on the broken-line curve (a distance $c_P\tau_m$). Accordingly, correction is performed for the angle $\theta$ on a voxel-by-voxel basis using $D_m(\theta) - c_P\tau_m$ as an amount of distortion (an amount of transformation in position of a voxel). Note that correction is not limited to correction using the correction table 92, and correction using a correction formula may be performed. After that, the image rendering unit 93 determines, using the correction table 92 and using image information that is obtained by image reconstruction, new image information in which distortion is corrected. The display section 10 displays the new image information. In this manner, the amounts of distortion can be quantitatively determined.

Figure 5B:
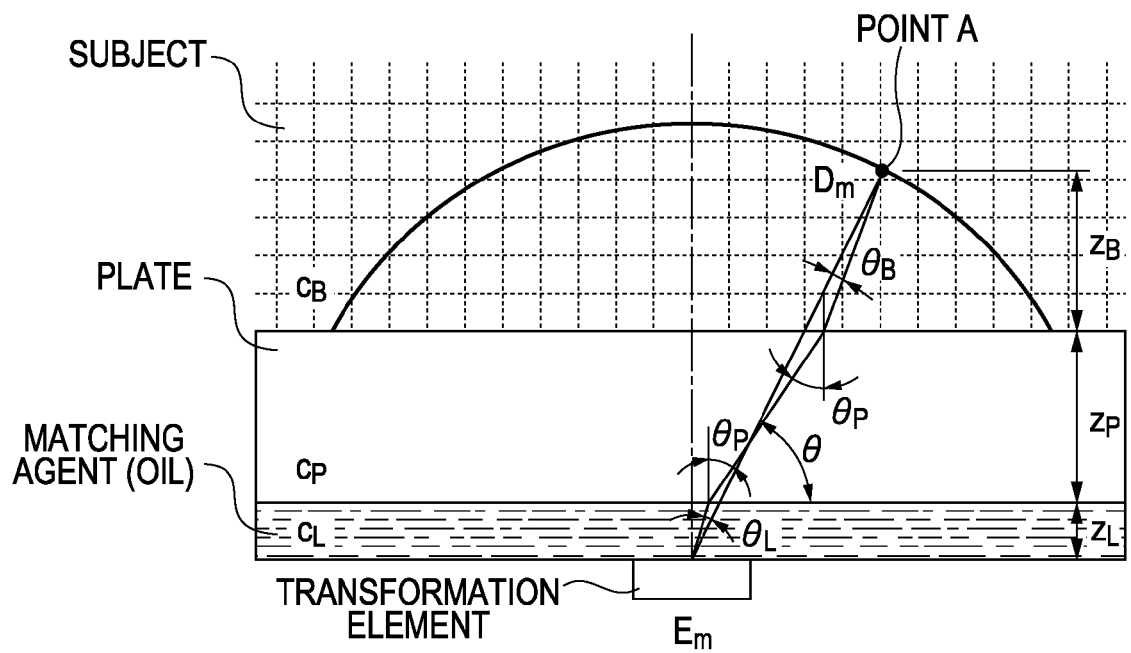
FIG. 5B is a schematic diagram for explaining image distortion associated with refraction using equations in the first embodiment of the present invention.

Note that, as described above, resolution is improved by performing correction for at least refraction that occurred at the interface between the subject and the plate 1. However, there is a case in which an acoustic matching agent, such as water or oil, is provided between the plate 1 and the probe 5 as shown in FIG. 5B. Furthermore, there is also a case in which an acoustic matching agent, such as a sonar gel, is provided between the plate 1 and the subject. Although the sound velocities in these acoustic matching agents are close to the sound velocity in the subject, preferably, correction is also performed for refractions that occurred at interfaces associated with the acoustic matching agents. More particularly, preferably, correction is performed for refraction caused by the acoustic matching agent that is provided between the plate 1 and the probe 5. In this case, referring to FIG. 5B, $D_m$ given above can be calculated using $D_m(\theta) = ((z_L \tan \theta_L + z_P \tan \theta_P + z_B \tan \theta_B)^2 + (z_L + z_P + z_B)^2)^{1/2}$ and using $\tan \theta = (z_L + z_P + z_B)/(z_L \tan \theta_L + z_P \tan \theta_P + z_B \tan \theta_B)$. In FIG. 5B, $z_L$ is a thickness of the acoustic matching agent, and $c_L$ is a sound velocity in the acoustic matching agent.

Furthermore, the arrival time $\tau_m$ of the photoacoustic wave is represented by $\tau_m = \tau_L + \tau_P + \tau_B$. $\tau_L$ is a propagation time taken for a photoacoustic wave to propagate through the acoustic matching agent, and is represented by $\tau_L = z_L/(c_L \cos \theta_L)$. Similarly, $\tau_P$ is a propagation time taken for a photoacoustic wave to propagate through the plate, and is represented by $\tau_P = z_P/(c_P \cos \theta_P)$. $\tau_B$ is a propagation time taken for a photoacoustic wave to propagate through the subject, and is represented by $\tau_B = z_B/(c_B \cos \theta_B)$. Using these equations, an amount of distortion caused by refraction can be calculated for the angle $\theta$ as a difference between a value that is obtained by multiplying $\tau_m$ by a sound velocity (for example, the sound velocity in the subject $c_B$) and $D_m(\theta)$. As described above, even when the number of interfaces at which refraction occurs is increased, the amounts of distortion can be geometrically determined. However, in the following description, a refraction that occurred between the subject and the plate 1 is described. The refraction is a refraction, from among refractions that result in a reduction in resolution, for which an effect of correction is the largest. Description regarding refraction caused by the acoustic matching agent that is provided between the plate 1 and the probe 5 or between the plate 1 and the subject is omitted.

Next, a correction method in a case in which correction is performed using the circular-back-projection in image reconstruction will be described with reference to FIG. 6. The circular-back-projection is an algorithm in which a circular arc (spherical) having a radius of a distance from a transformation element of the probe 5 to a sound source is drawn using a time $\tau$ at which the transformation element received a photoacoustic wave, in which each of circular arcs is drawn for a corresponding one of the transformation elements in the same manner, and in which imaging of an intersection of the circular arcs as the source (the source that generated the photoacoustic wave) is performed. If the sound velocity does not change in both the subject and the plate 1 (the sound velocity in this case is denoted by c), a point A of intersection of the broken lines is determined as an intersection, and image reconstruction is performed using the point A as a sound source. However, in reality, because the sound velocity in the plate 1 is higher than the sound velocity in the subject, a photoacoustic wave is refracted at the interface between the plate and the subject. Accordingly, the sound source is a point B (the point B of intersection of the solid lines should be determined as an intersection). As described with reference to FIG. 5A, the position of the point B can be determined by calculation. The point A can also be determined by calculation because the point A is a point at which circular arcs having radiuses of $c \cdot \tau_i$ overlap one another. However, in reality, because the sound velocity in the subject is different from the sound velocity in the plate 1, circular arcs indicated by the dotted lines do not completely overlap one another as shown in FIG. 5A. In FIG. 5A, an intersection is schematically indicated by the point A.

In this manner, a relationship between the position of the point A with respect to the point B and regions is determined in advance, and the point A which is determined supposing that the sound velocity does not change is shifted to the position of the point B, whereby image information in which correction is performed for refraction that occurred due to the difference between the sound velocity in the subject and the sound velocity in the plate 1 can be acquired. In other words, amounts of transformation in positions of all of the voxels are summarized in the correction table 92 so that the point A can be moved to the position of the point B. Accordingly, after image reconstruction is performed supposing that the sound velocity does not change, new image information, i.e., image information in which correction is performed for refraction that occurred due to the difference between the sound velocity in the subject and the sound velocity in the plate 1, can be acquired. Note that, although, regarding the image reconstruction method, the circular-back-projection is described, the image reconstruction method is not limited thereto. The same correction table 92 can also be applied in other image reconstruction methods including an image reconstruction method using the time-domain algorithm and an image reconstruction method using the Fourier-domain algorithm.

Note that, although the description above is made under the assumption that the plate 1 is a flat plate, the plate is not limited to a flat plate. Regarding the flatness of the plate, even when the surface of the plate has a curvature, the plate is effective. Note that, when the surface of the plate 1 has a curvature, preferably, an incident angle corresponding to the curvature reflects in the correction table 92 or the correction formula. Furthermore, the description with reference to FIG. 1 is made under the assumption that the plates 1 are two flat parallel plates. However, the above-described biological information acquisition apparatus can be applied to a case in which one of the plates 1 is provided between the subject and the probe 5. The use of the plates 1 is not limited to compression of the subject.

As described above, the correction table 92 or the correction formula is provided in advance, whereby not only image distortion associated with refraction of a photoacoustic wave can be corrected but also complicated calculation for performing correction for refraction in a case of image reconstruction becomes unnecessary, so that a calculation time can be reduced.

Second Embodiment

The PAM apparatus that operates using the PAT as a principle is described in the first embodiment. In the second embodiment, a configuration of an ultrasound apparatus and a processing method in a case in which the PAT is applied to the ultrasound apparatus are described. Even in a case of an ultrasound apparatus that transmits/receives an ultrasound wave to/from a subject, when a plate is provided between an ultrasound probe and the subject, a transmitted ultrasound wave is refracted. A typical ultrasound apparatus does not transmit/receive an ultrasound wave via a plate to a subject. However, when a case in which an ultrasound probe is provided in parallel to the probe 5 of the PAM apparatus shown in FIG. 1, or a case in which an ultrasound probe is provided on a compression plate of an X-ray mammography apparatus is supposed, it is necessary to consider refraction that occurs because of the difference between a sound velocity in the subject and a sound velocity in the plate. Supposing such a case, FIG. 7 is a diagram illustrating a signal flow of a process sequence from transmission of an ultrasound wave from an ultrasound probe toward a subject to reception of the ultrasound wave, which is reflected by the subject, and imaging.

Figure 7:
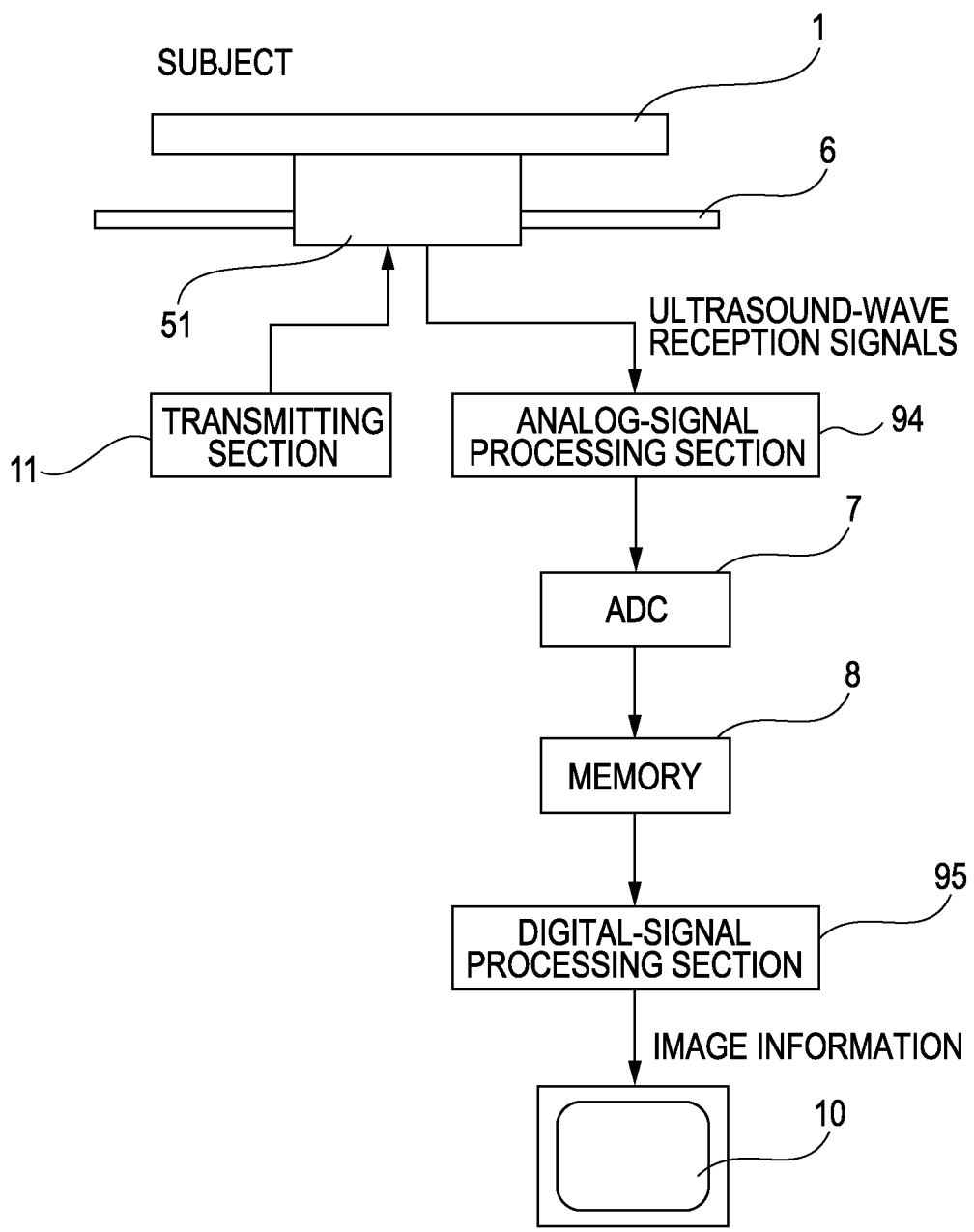
FIG. 7 is a schematic diagram for explaining a signal processing section in a second embodiment of the present invention.

Referring to FIG. 7, a transmitting section 11 performs a process such as a transmission beamforming process for transmitting an ultrasound wave. An ultrasound probe 51 transmits/receives an ultrasound wave in accordance with a transmission signal from the transmitting section 11. An analog-signal processing section 94 performs a filtering process and an amplification process. The ADC 7 digitizes analog signals that have been subjected to signal processing by the analog-signal processing section 94, thereby obtaining digital signals. The memory 8 stores the digital signals (reception signals) as a time series. A digital-signal processing section 95 acquires image information using the reception signals stored in the memory 8, and causes the display section 10 to display the image information.

Figure 8:
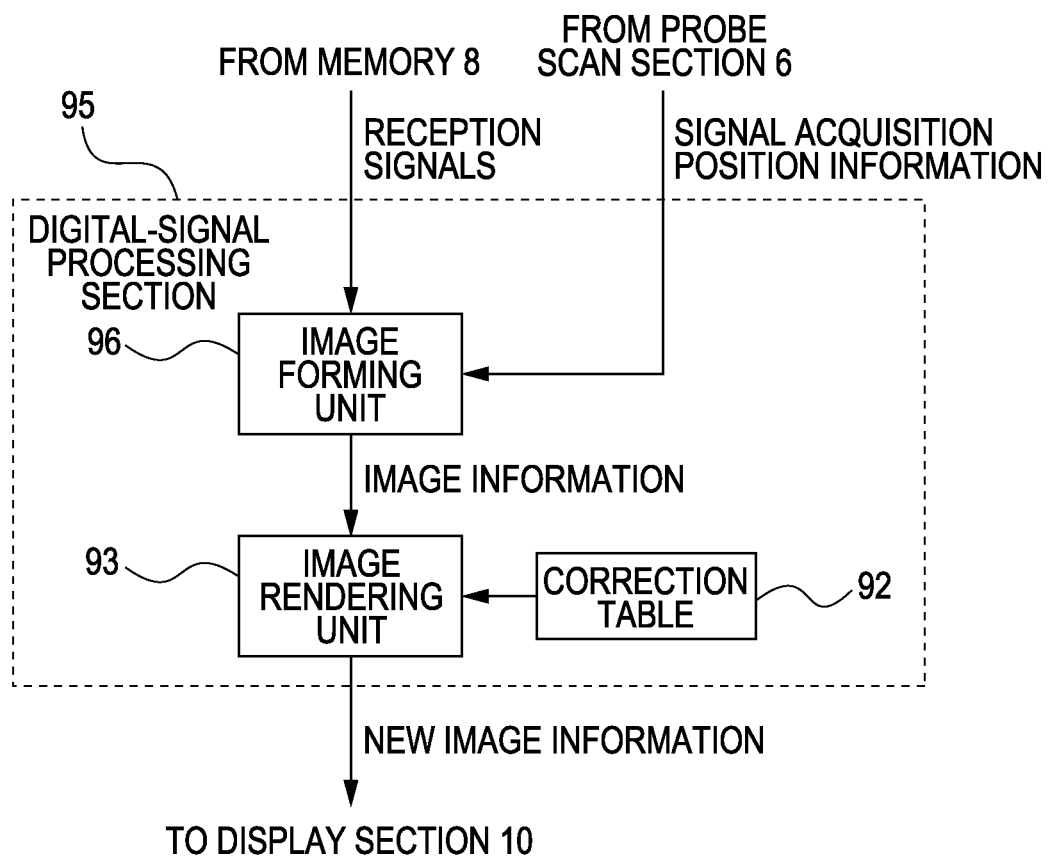
FIG. 8 is a schematic diagram for explaining a processing unit that acquires new image information in the second embodiment of the present invention.
Figure 9:
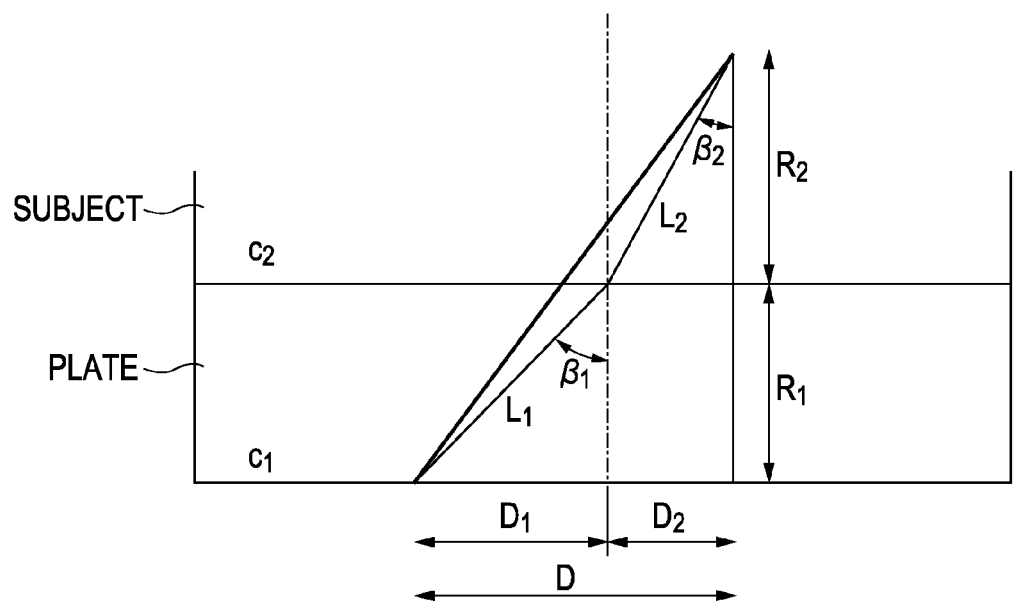
FIG. 9 is a schematic diagram for explaining the background art.

In a case of an ultrasound apparatus, the digital-signal processing section 95 has a configuration shown in FIG. 8. In FIG. 8, an image forming unit 96 performs a reception beamforming process on the reception signals stored in the memory 8. The reception beamforming process includes detection of an ultrasound echo, processing using the delay-and-sum, and so forth. The image forming unit 96 performs signal processing, such as compression using logarithm, and performs image processing. In this case, for delay times in a case of processing using the delay-and-sum, it is not necessarily necessary to consider the difference between the sound velocity in the subject and the sound velocity in the plate 1. Furthermore, when the ultrasound probe 51 is configured as a two-dimensional array, image information that is obtained by the image forming unit 96 is three-dimensional image information. When the ultrasound probe 51 is configured as a one-dimensional array, image information that is obtained by the image forming unit 96 is two-dimensional image information. Moreover, two-dimensional information items are connected together in accordance with the signal acquisition position information that is supplied from the probe scan section 6, whereby a three-dimensional image information item can be acquired. Additionally, the correction table 92 is provided as a table in which the amounts of distortion of the individual voxels (or the individual image elements) (the amounts of transformation in positions of the individual voxels) are summarized. The image rendering unit 93 corrects image information that is supplied by the image forming unit 96. Note that the method which is described with reference to FIG. 5A in the first embodiment can be applied as a method for determining the amounts of correction to be summarized in the correction table 92, and the amounts of correction can be geometrically determined in accordance with Snell's law. Furthermore, as in the case of the first embodiment, correction is not limited to correction using the correction table 92, and the correction formula may be used.

As described above, according to the second embodiment, even in a case of the ultrasound apparatus, image information is acquired without consideration of refraction of an ultrasound wave that occurred because of the difference between the sound velocity in the subject and the sound velocity in the plate 1, and then, the image information is corrected on an image-element-by-image-element basis in accordance with the correction table 92 or the correction formula, whereby image distortion can be reduced.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2008-330364, filed Dec. 25, 2008 and No. 2009-239399, filed Oct. 16, 2009, which are hereby incorporated by reference herein in their entirety.

The invention claimed is:

1. A subject information acquisition apparatus comprising:
   a subject holding member configured to hold a subject;
   a probe having a plurality of transformation elements and configured to receive an acoustic wave emitted from the subject through the subject holding member, and to convert the acoustic wave into electric signals;
   a processing section configured to generate first image data using the electric signals, and
   a sound-velocity measurement section configured to obtain a sound velocity of the acoustic wave in the subject, wherein the sound-velocity measurement section obtains the sound velocity in the subject by using a time from when an ultrasound wave is transmitted from the probe to when a reflected ultrasound wave is received, a thickness of the subject in which the ultrasound wave transmitted from the probe propagates, a sound velocity in the subject holding member, and thickness of the subject holding member,
   wherein the processing section has a correction table or a correction formula based on the sound velocity obtained by the sound-velocity measurement section and the sound velocity in the subject holding member, for performing correction of refraction of the acoustic wave that has occurred due to a difference between the sound velocity in the subject and the sound velocity in the subject holding member,
   wherein the processing section corrects information regarding image element location of the first image data by shifting the image element location of the first image data in accordance with an amount of transformation in position of individual image elements caused by refraction of the acoustic wave, based on the correction table or the correction formula, and
   wherein the processing section obtains second image data in accordance with the shifted image element location of the first image data.

2. The subject information acquisition apparatus according to claim 1, wherein the acoustic wave is a photoacoustic wave that is emitted by irradiating the subject with light, and the probe receives the photoacoustic wave.

3. The subject information acquisition apparatus according to claim 1, wherein the acoustic wave is an ultrasound wave that is transmitted to the subject, that is reflected inside the subject, and is returned, and the probe receives the reflected and returned ultrasound wave.

4. The subject information acquisition apparatus according to claim 1, wherein amounts of transformation in positions of individual image elements are stored as the correction table or the correction formula in the processing section, the amounts of transformation in positions of individual image elements being calculated in accordance with Snell's law using a thickness of the subject holding member, the sound velocity in the subject holding member, and the sound velocity in the subject.

5. The subject information acquisition apparatus according to claim 1, wherein the first image data is generated by reconstruction using the electric signals.

6. The subject information acquisition apparatus according to claim 1, wherein the subject holding member comprises two plates which sandwich the subject, and
wherein the sound-velocity measurement section obtains the sound velocity in the subject by using a distance between the plates as the thickness of the subject.

7. A subject information acquisition method comprising:
receiving, at a probe having a plurality of transformation elements, an acoustic wave emitted from a subject through a subject holding member;
converting the acoustic wave into electric signals;
generating first image data using the electric signals;
obtaining a sound velocity of the acoustic wave in the subject by using a time from when an ultrasound wave is transmitted from the probe to when a reflected ultrasound wave is received, a thickness of the subject in which the ultrasound wave transmitted from the probe propagates, a sound velocity in the subject holding member, and thickness of the subject holding member;
storing a correction table or a correction formula based on the sound velocity obtained and on the sound velocity in the subject holding member for
performing correction of refraction of the acoustic wave that has occurred due to a difference between the sound velocity in the subject and the sound velocity in the subject holding member by using the correction table or the correction formula;
correcting information regarding image element location of the first image data by shifting the image element location of the first image data in accordance with an amount of transformation in position of individual image elements caused by the refraction of the acoustic wave based on the correction table or the correction formula; and
generating second image data using the shifted image element location of the first image data.

8. The subject information acquisition method according to claim 7, further comprising:
irradiating the subject with light,
wherein the acoustic wave is a photoacoustic wave generated by the light irradiated to the subject.

9. The subject information acquisition method according to claim 8, further comprising:
transmitting an ultrasound wave to the subject,
wherein the acoustic wave is the ultrasound wave which is transmitted to the subject and reflected within the subject.

10. The subject information acquisition method according to claim 8, wherein the correction table or the correction formula is a table or a formula indicating a position transformation amount for each image element calculated based on Shell's law using a thickness of the subject holding member, the sound velocity in the subject, and the sound velocity in the subject holding member.

11. The subject information acquisition method according to claim 7, wherein the first image data is generated by reconstruction using the electric signals.

12. The subject information acquisition method according to claim 7, wherein the correction table or the correction formula includes calculation results of amounts of transformation in positions of individual image elements of the first image data.

* * * * *